United States Patent
Doi et al.

(10) Patent No.: US 10,828,279 B2
(45) Date of Patent: Nov. 10, 2020

(54) PROPHYLACTIC AND/OR THERAPEUTIC DRUG FOR DIABETIC NEPHROPATHY

(71) Applicants: HuBit genomix, Inc., Tokyo (JP); Fuso Pharmaceutical Industries, Ltd., Osaka (JP)

(72) Inventors: Toshio Doi, Kyoto (JP); Tatsuya Tominaga, Tokushima (JP); Yui Fujita, Tokushima (JP)

(73) Assignees: HUBIT GENOMIX, INC., Tokyo (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/372,571

(22) Filed: Apr. 2, 2019

(65) Prior Publication Data

US 2019/0314339 A1    Oct. 17, 2019

(30) Foreign Application Priority Data

Apr. 2, 2018  (JP) .................................. 2018-071111

(51) Int. Cl.
| | |
|---|---|
| *A61K 31/415* | (2006.01) |
| *A61P 13/12* | (2006.01) |
| *A61K 31/192* | (2006.01) |
| *A61K 31/167* | (2006.01) |
| *A61K 9/00* | (2006.01) |

(52) U.S. Cl.
CPC .......... *A61K 31/415* (2013.01); *A61K 9/0019* (2013.01); *A61K 9/0053* (2013.01); *A61K 31/167* (2013.01); *A61K 31/192* (2013.01); *A61P 13/12* (2018.01)

(58) Field of Classification Search
CPC .. A61K 31/167; A61K 31/192; A61K 31/415; A61K 9/0019; A61K 9/0053; A61P 31/12
See application file for complete search history.

(56) References Cited

FOREIGN PATENT DOCUMENTS

| WO | WO-2007113122 A1 * | 10/2007 | ........... C07D 231/12 |
| WO | WO-2013052647 A2 * | 4/2013 | ............. A61K 31/19 |

OTHER PUBLICATIONS

Adler et. al., Kidney International, 2000, vol. 57, pp. 2084-2092 (Year: 2000).*
Mi et. al., Journal of Molecular Endocrinology, 2016, vol. 57, pp. 233-249 (Year: 2016).*
Ritz et al., European Journal of Clinical Investigation, 2005, vol. 35(suppl. 3), pp. 66-74 (Year: 2005).*

* cited by examiner

*Primary Examiner* — Sarah Pihonak
(74) *Attorney, Agent, or Firm* — Morgan, Lewis & Bockius LLP

(57) ABSTRACT

The present invention provides a drug capable of preventing or treating diabetic nephropathy.
The present invention relates to a prophylactic and/or therapeutic drug for diabetic nephropathy, comprising a RARγ agonist as an active ingredient. The present invention also provides a prophylactic and/or therapeutic drug for renal anemia; a drug inhibiting the expression of type IV collagen in mesangial cells; a drug inhibiting the expression of BMP4 in mesangial cells; and a drug inhibiting fibrosis in the renal tubulointerstitium.

17 Claims, 6 Drawing Sheets

PROPHYLACTIC AND/OR THERAPEUTIC DRUG FOR DIABETIC NEPHROPATHY

FIELD OF THE INVENTION

The present invention relates to a prophylactic and/or therapeutic drug for diabetic neuropathy.

BACKGROUND OF THE INVENTION

Sugars such as starch (carbohydrates) are one of the most critical nutrients for maintaining our lives. Sugars are degraded to produce glucose, which is taken into cells of the whole body from the blood and used as a major energy source. Glucose in the blood is referred to as blood glucose. Blood glucose level rises when carbohydrates have been taken into the body after meal or the like. On the other hand, blood glucose level decreases when glucose has been consumed as energy by exercise or the like. In healthy persons, blood glucose levels are controlled within a specific range through balancing between insulin and hormones which have an opposite effect to that of insulin. Therefore, their blood glucose levels do not change drastically even after meal or exercise.

Diabetes mellitus (commonly called diabetes) is a state in which blood glucose levels have been increased because glucose is not used effectively due to insufficient action of insulin. When left untreated, this state generates various effects. Diabetes is classified into four types depending of the causative; type 1 diabetes, type 2 diabetes, other diabetes due to specific causes and gestational diabetes. Of these, type 2 diabetes is the most important considering the number of patients.

Type 2 diabetes is caused by insufficient secretion or function of insulin. Type 2 diabetes is mainly seen in persons of middle or older age, but onset in the young is increasing recently. In Japan, about 90% of diabetic patients are diagnosed as suffering from type 2 diabetes. It is generally recognized that type 2 diabetes is developed due to hereditary constitution combined with lifestyle factors (such as overeating, especially that of high-fat diet, lack of physical activity, or stress), as well as aging. Even non-obese persons are prone to develop type 2 diabetes if they are in a condition of the so-called metabolic syndrome involving increased visceral fat.

Since type 2 diabetes develops unknowingly and progresses slowly, it may have progressed asymptomatically. If such type 2 diabetes is left without blood glucose control, the complications described below will occur.

Complications may be roughly divided into microangiopathy and macroangiopathy. Microangiopathy is a complication characteristic of diabetes seen in small blood vessels and consists of three types, i.e., diabetic retinopathy, diabetic nephropathy and diabetic neuropathy (these are called three major complications of diabetes). Macroangiopathy is a complication caused by arteriosclerosis (disorder of large blood vessels) and classified into apoplexy, myocardial infarction and peripheral arterial disease (e.g., gangrene in the feet).

According to 2016 "National Health and Nutrition Survey" conducted by Ministry of Health, Labour and Welfare (seikatsusyukanbyo.com/statistics/2017/009436.php) (Non-Patent Document No. 1), the rate of "persons who are strongly suspected to be diabetic" was 12.1%, giving an estimate of about 10 million. The rate of "persons from whom the possibility of diabetes cannot be excluded" was also 12.1%, again giving an estimate of about 10 million. Briefly, the number of persons with diabetes and that of persons at risk of diabetes were each estimated about 10 million.

According to a publication by International Diabetes Federation (IDF) (Diabetes Atlas Seventh Edition: diabetesatlas.org) (Non-Patent Document No. 2), the diabetic population in the world is growing explosively. As of 2015, the estimated number of people with diabetes amounted to 415 million, showing an increase of 28.3 million from the previous year. If effective measures are not taken, IDF predicts, the number will increase to 642 million by 2040. In 2015, the prevalence rate of diabetes in adults aged 20-79 was estimated 8.8%, which means one in eleven adults is diabetic. Diabetes-associated medical costs are about 673 billion dollars, which accounts for 5-20% of the total medical costs in major countries in the world. It is predicted that medical costs for diabetes will increase to 802 billion dollars by 2040.

DESCRIPTION OF THE RELATED ART

As described above, the explosive increases in diabetic patients and medical costs have become a great issue in the world. Under these circumstances, various therapeutics for diabetes have been developed. Among them, major treatments of diabetics include blood glucose control and antihypertensive therapy. Although the basics of blood glucose control are low calorie meal and exercise therapy, there may also be performed administration of diabetic drugs (e.g., DPP-4 inhibitors, GLP-1 receptor agonists, SGLT2 inhibitors, SU agents, α-glucosidase inhibitors, biguanide, rapid-acting-type insulin secretion promoters, insulin resistance ameliorating agents, or combined drugs) or insulin injection. Antihypertensive therapy comprises administration of angiotensin-converting enzyme (ACE) inhibitors or angiotensin II receptor antagonists (ARBs), and optionally comprises administration of other types of antihypertensives such as calcium antagonists or diuretic drugs.

On the other hand, among the three major complications of diabetes mentioned above, diabetic nephropathy causes severe, life-threatening conditions such as renal failure or uremia, when its symptoms have progressed to cause accumulation of waste products in the blood. Eventually, a patient who has developed renal failure needs hemodialysis. According to recent data for the cases in which patients are newly introduced to hemodialysis, diabetic nephropathy accounts for more than 40% of the underlying diseases (jsdt.or.jp/overview_confirm.html) (Non-Patent Document No. 3) and this rate has remained almost on the same level since 2008 (Illustrated Guidebook: Status of Chronic Dialysis Therapy in Japan as of Dec. 31, 2014, published by Japanese Society for Dialysis Therapy on Dec. 1, 2015).

In Japan, patients on dialysis amounted to about 320,000 as of 2016, with a yearly increase of 5000 since then. The rate of increase in the number of patients is almost equal to the rate at which Japanese people grow older, and it is predicted that the patient number will increase continuously up to 2025. The National Treasury is bearing an annual cost of about 5 million Yen per patient on dialysis, which by simple calculation means bearing 1600 billion Yen in total. Further, patients on dialysis have a high chance of developing complications, so taking this fact into consideration, the medical cost expended for patients on dialysis amounts to about 2000 billion yen (5% of the total medical cost in Japan). Therefore, to inhibit the number of patients on dialysis has become one of the urgent problems in medical economics.

Under such circumstances, the following drugs have been reported for use in the treatment of diabetic nephropathy but their effects are by no means satisfactory: growth hormone (GH)/insulin-like growth factor (IGF1) inhibitors (Curr Diabetes Rev (2011) 7(1) 50 (Non-Patent Document No. 4)), Jak/Stat inhibitors (Diabetologia (2016) 59,1624 (Non-Patent Document No. 5); Diabetes (2009) 58, 469 (Non-Patent Document No. 6); Nephrol Dial Transplant (2015) 30, iv54 (Non-Patent Document No. 7)), CCL2=MCP1/CCR2 antagonists (Biochem Biophys Res Commun (2007) 360, 772 (Non-Patent Document No. 8); Diabetes Care (2009) 32(3) 465 Non-Patent Document No. 9)), Nrf2-Keap1 activators (N Engl J Med (2013) 369 (26) 2492 (Non-Patent Document No. 10); Nephrol Dial Transplant (2013) 28, 2841 (Non-Patent Document No. 11); N Engl J Med (2011) 365 (4) 327 (Non-Patent Document No. 12); Am J Physiol Renal Physiol (2013) 304, F808 (Non-Patent Document No. 13)), Notch1 inhibitors (Nephrol Dial Transplant (2015) 30, iv54 (Non-Patent Document No. 7)), and ETAR antagonists (Nephrol Dial Transplant (2015) 30, iv54 (Non-Patent Document No. 7)).

PRIOR ART LITERATURE

Non-Patent Documents

Non-Patent Document No. 1: Ministry of Health, Labor and Welfare, "The number of persons with diabetes and that of persons at risk of diabetes were each estimated about 10 million." 2017 (seikatsusyukanbyo.com/statistics/2017/009436.php)

Non-Patent Document No. 2: International Diabetes Federation (IDF) (Diabetes Atlas Seventh Edition) 2015 (diabetesatlas.org/)

Non-Patent Document No. 3: Japanese Society for Dialysis Therapy, Illustrated Guidebook: Status of Chronic Dialysis Therapy in Japan as of Dec. 31, 2014, published by Japanese Society for Dialysis Therapy on Dec. 1, 2015) 2015 (jsdt.or.jp/overview_confirm.html).

Non-Patent Document No. 4: Kumar P A, Brosius F C, Menon R. The Glomerular Podocyte as a Target of Growth Hormone Action: Implications for the Pathogenesis of Diabetic Nephropathy. Current Diabetes Reviews 2011; 7(1):50-55.

Non-Patent Document No. 5: Brosius F C, Tuttle K R, Kretzler M. JAK inhibition in the treatment of diabetic kidney disease. Diabetologia 2016; 59(8):1624-1627.

Non-Patent Document No. 6: Berthier C C, Zhang H, Schin M L, et al. Enhanced Expression of Janus Kinase-Signal Transducer and Activator of Transcription Pathway Members in Human Diabetic Nephropathy. Diabetes 2009; 58(2):469-477.

Non-Patent Document No. 7: Zoja C, Zanchi C, Benigni A. Key pathways in renal disease progression of experimental diabetes. Nephrology, dialysis, transplantation 2015; 30(iv):54-59.

Non-Patent Document No. 8: Kanamori H, Matsubara T, Mima A, et al. Inhibition of MCP-1/CCR2 pathway ameliorates the development of diabetic nephropathy. Biochemical and Biophysical Research Communications 2007; 360(4):772-777.

Non-Patent Document No. 9: Zineh I, Beitelshees A L, Silverstein J H, et al. Serum Monocyte Chemoattractant Protein-1 Concentrations Associate With Diabetes Status but Not Arterial Stiffness in Children With Type 1 Diabetes. Diabetes Care 2009; 32(3):465-467.

Non-Patent Document No. 10: de Zeeuw D, Akizawa T, Audhya P, et al. Bardoxolone Methyl in Type 2 Diabetes and Stage 4 Chronic Kidney Disease. The New England Journal of Medicine 2013; 369(26):2492-2503.

Non-Patent Document No. 11: Heerspink H J L, Chertow G M, Akizawa T, et al. Baseline characteristics in the Bardoxolone methyl EvAluation in patients with Chronic kidney disease and type 2 diabetes mellitus: the Occurrence of renal eveNts (BEACON) trial. Nephrology, dialysis, transplantation 2013; 28(11):2841-2850.

Non-Patent Document No. 12: Pergola P E, Raskin P, Toto R D, et al. Bardoxolone Methyl and Kidney Function in CKD with Type 2 Diabetes. The New England Journal of Medicine 2011; 365(4):327-336.

Non-Patent Document No. 13: Zoja C, Coma D, Nava V, et al. Analogs of bardoxolone methyl worsen diabetic nephropathy in rats with additional adverse effects. American journal of physiology. Renal physiology 2013; 369(26): F808-819.

SUMMARY OF THE INVENTION

The object of the present invention is providing a drug capable of preventing or treating diabetic nephropathy.

Based on the pathogenic mechanism of diabetic nephropathy the inventors found, they have explored therapeutics for diabetic nephropathy and found candidate compounds for such therapeutics. Thus, the present invention has been achieved.

Diabetic nephropathy is one of microvascular diseases caused by chronic exposure to hyperglycemia. Pathologically, diabetic nephropathy presents thickness of the glomerular blood-vessel basement membrane and expansion of the mesangial area; clinically, diabetic nephropathy presents symptoms such as proteinuria (microalbuminuria), hypertension, edema, etc., eventually resulting in renal failure from glomerulosclerosis lesions. Further, in diabetes, abnormalities such as arteriolosclerosis and tubulointerstitial degeneration/fibrosis are also observed in tissues other than the glomeruli, which exacerbates the glomerular lesions still further. Briefly, a pathological condition in which proteinuria, hypertension and renal dysfunction gradually progress after a certain period of diabetes duration can be defined as nephropathy. The present inventors have proven that a nuclear transcription factor Smad1 which is a molecule downstream of ALK (activating receptor-like kinase), a type I receptor in the TGF-β superfamily, is a direct transcriptional activator of type IV collagen α1, α2 chain genes and that this is the most critical causative molecule for glomerular mesangial matrix expansion in diabetic nephropathy.[1,2] In STZ (streptozotocin)-induced diabetic rats, Smad1 is the most critical factor to cause mesangial matrix expansion.[3] Further, using diabetic animal models, the present inventors have shown in various studies that Smad1 signaling pathways are strongly associated with the pathogenesis of the disease.[4-10]

Still further, the present inventors have found that activation of Smad1 signaling pathways through BMP4 (bone morphogenetic protein 4)/ALK3 signaling pathways play a key role in mesangial matrix expansion which is a pathological feature in diabetic nephropathy.[11] Hereinbelow, the involved mechanism of action will be described in detail. Prolonged exposure to hyperglycemia increases AGEs (advanced glycation end products) in the blood. When these AGEs in the blood bind AGE receptors on mesangial cells, BMP4 production in mesangial cells increases. Subsequently, when BMP4 binds ALK3 receptors on mesangial cells, phosphorylation of Smad1 occurs. Two molecules of phosphorylated Smad1 (pSmad1) and one molecule of Smad4 form a trimer. The timer moves from the cytoplasm into the nucleus and initiates the transcription of type IV collagen, one of its target genes. As a result, an increase in the production of this type IV collagen leads to mesangial matrix expansion (FIG. 1).

Based on the above-mentioned mechanism of action, it is believed that a compound capable of inhibiting the BMP4/ALK3/Smad1/type IV collagen signaling pathways can be a prophylactic and/or therapeutic drug for diabetic nephropathy. BMP4/ALK3 is a member of the TGF-β superfamily.[11] Recently, it has been reported that RAR (retinoic acid receptor) agonists inhibit TGF-β signal transductions.[12] In view of what have been described so far, the present inventors have planned to evaluate inhibitory activities of various RAR agonists.

RAR has three subtypes, α, β and γ. Compounds with RAR agonist activity having specificity or selectivity for the subtypes are expected to reduce the risk of side effects (Patent Document No. 1). Among such compounds, RARα agonists such as retinoid or 4-[(5,6,7,8-tetrahydro-5,5,8,8-tetramethyl-2-naphthalenyl)carbamoyl]benzoic acid are disclosed as a pharmaceutical for preventing and/or treating diabetic retinopathy or age-related macular degeneration (see Patent Documents Nos. 2, 3 and 4). In contrast, RARγ agonists represented by palovarotene are shown to be useful for pulmonary emphysema, cancer and skin diseases (Patent Document No. 5) and for neural pain (Patent Document No. 6). Palovarotene is also useful for muscle repair as disclosed in Patent Document No. 7. However, to date, there are no reports to examine the effect of palovarotene on diabetic nephropathy and no documents that suggest such effect.

On the other hand, in diabetes-induced tubulointerstitium lesions, TGF-β phosphorylates Smad2/3 to elicit αSMA and induce fibrosis.[13, 14] Tubulointerstitium lesions are an advanced pathological condition of diabetic nephropathy. A preceding study has shown that "hyperglycemia and subsequent glomerular hyperfiltration as well as hemodynamic abnormalities such as hypertension that are frequently complicated with diabetes will eventually accelerate the decrease of nephron number and histological changes such as fibrosis of the renal interstitium, leading to the progress of renal failure."[15]

Like glomerular lesion, tubulointerstitium lesion is one of the critical pathological conditions of diabetic nephropathy. However, in the search of prophylactic/therapeutic drugs for diabetic nephropathy so far conducted, few attempts have been made to explore more effective prophylactic/therapeutic drugs by simultaneously evaluating glomerular and tubulointerstitial lesions. Under the circumstances, the present inventors constructed an in vitro evaluation system using cultured mesangial cells, and explored small molecule compounds, mostly comprising RARγ agonists, that inhibit BMP4/ALK3/Smad1/type IV collagen signaling pathways or the phosphorylation of Smad2/3. As a result, the present inventors have found that RARγ agonists are capable of inhibiting these signaling pathways or the phosphorylation. Thus, the present invention has been achieved. Compounds capable of inhibiting BMP4/ALK3/Smad1/type IV collagen signaling pathways or the phosphorylation of Smad2/3 are useful in preventing and/or treating diabetes-associated complications, with in particular, diabetic nephropathy.

Further, a mechanism common to both the progress of interstitial fibrosis and the development of renal anemia has recently been assumed because fibroblasts constituting lesions of tubulointerstitial fibrosis (at least part of such fibroblasts) are derived from erythropoietin (EPO) producing cells and lose their EPO production capacity upon transformation into fibroblasts.[14] According to this hypothesis, it is believed that a prophylactic and/or therapeutic drug for interstitial fibrosis can potentially be an effective prophylactic and/or therapeutic drug for renal anemia.

The gist of the present invention is as described below.
(1) A prophylactic and/or therapeutic drug for diabetic nephropathy, comprising a RARγ agonist as an active ingredient.
(2) The prophylactic and/or therapeutic drug of (1) above, wherein the RARγ agonist is at least one compound selected from the group consisting of palovarotene, 3-fluoro-4-(2-hydroxy-2-(5,5,8,8-tetramethyl-5,6,7,8,-tetrahydronaphthalen-2-yl)acetamido)benzoic acid, 4-[7-(1-adamantyl)-6-hydroxynaphthalen-2-yl]benzoic acid, esters thereof and salts thereof.
(3) The prophylactic and/or therapeutic drug of (1) above, wherein diabetic nephropathy is derived from type 2 diabetes.
(4) A prophylactic and/or therapeutic drug for renal anemia, comprising a RARγ agonist as an active ingredient.
(5) A drug that inhibits the expression of type IV collagen in mesangial cells, comprising a RARγ agonist as an active ingredient.
(6) The drug of (5) above, wherein the RARγ agonist is at least one compound selected from the group consisting of palovarotene, 4-[7-(1-adamantyl)-6-hydroxynaphthalen-2-yl]benzoic acid, esters thereof and salts thereof.
(7) A drug that inhibits the expression of BMP4 in mesangial cells, comprising a RARγ agonist as an active ingredient.
(8) The drug of (7) above, wherein the RARγ agonist is at least one compound selected from the group consisting of palovarotene, 3-fluoro-4-(2-hydroxy-2-(5,5,8,8-tetramethyl-5,6,7,8,-tetrahydronaphthalen-2-yl)acetamido)benzoic acid, esters thereof and salts thereof.
(9) A drug that inhibits fibrosis in the renal tubulointerstitium, comprising a RARγ agonist as an active ingredient.
(10) The drug of (9) above, wherein the RARγ agonist is at least one compound selected from palovarotene, esters thereof and salts thereof.
(11) The drug of (9) above, which inhibits the expression of pSmad2/3 in the renal tubulointerstitial cells.
(12) The drug of (9) above, wherein fibrosis in the renal tubulointerstitium is derived from diabetic nephropathy.
(13) The drug of any one of (1) to (12) above, which is to be administered orally or parenterally.

EFFECT OF THE INVENTION

RARγ agonists (especially palovarotene, esters thereof and salts thereof) which are the active ingredient of the prophylactic and/or therapeutic drug for diabetic nephropathy of the present invention are capable of inhibiting fibrosis in renal tubulointerstitium, are useful in preventing the onset of diabetic nephropathy or in treating the same, and are potentially capable of preventing transition to hemodialysis.

Figure 1:
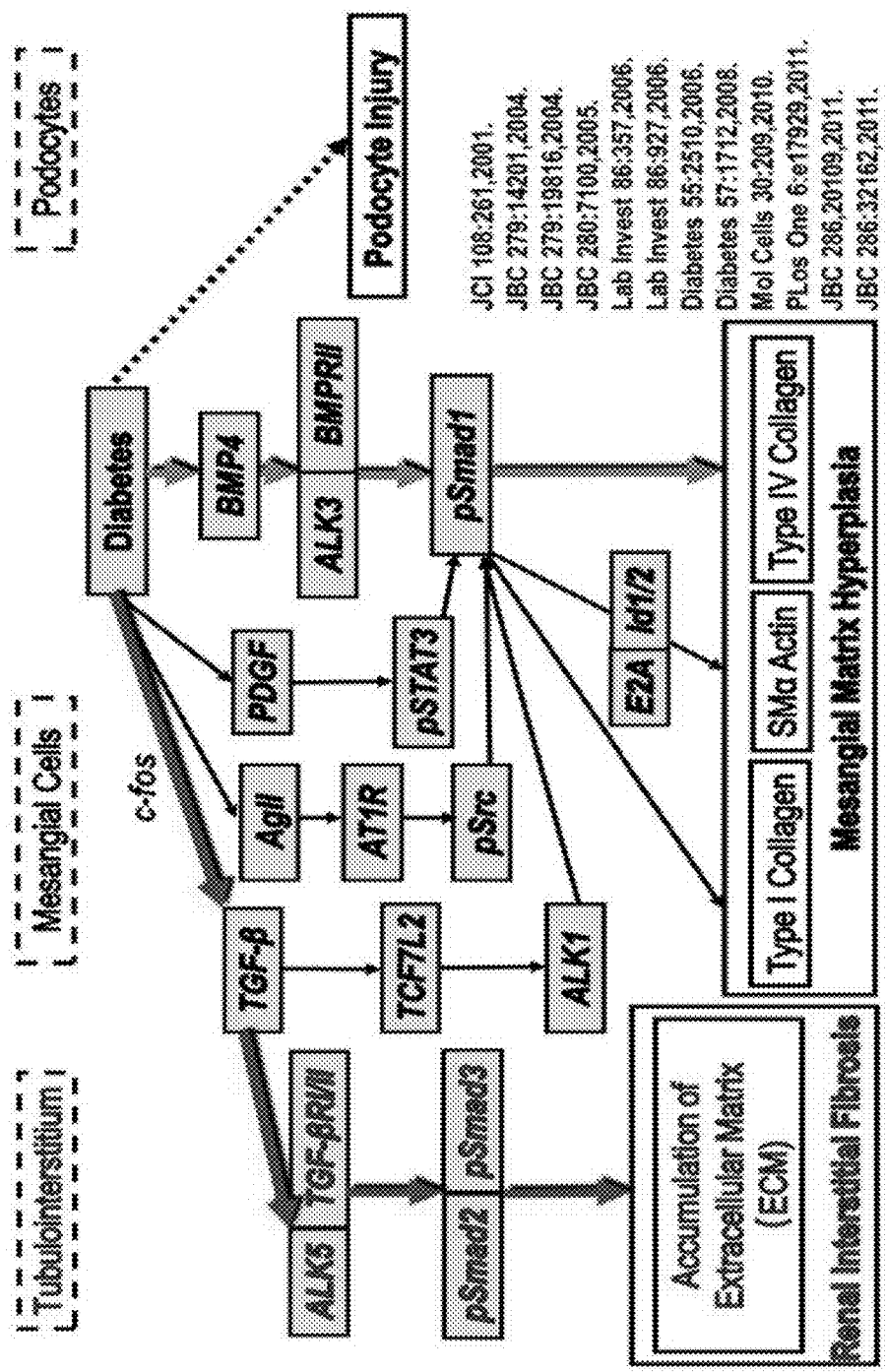
FIG. 1 is a schematic diagram showing the molecular mechanism of the onset of diabetic nephropathy.
Figure 2A:
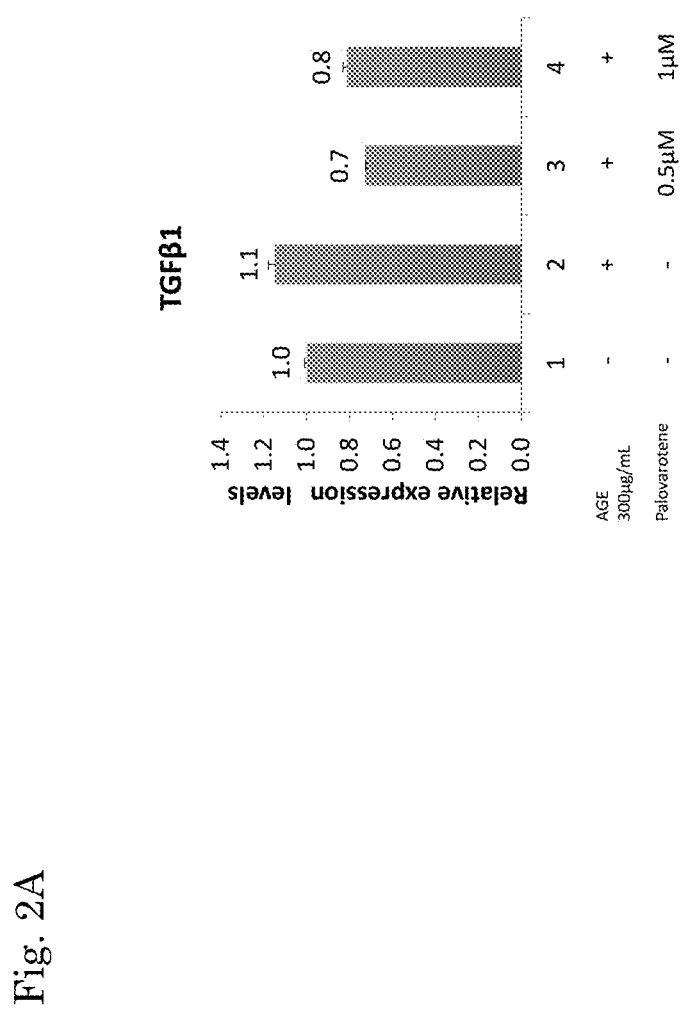
FIG. 2A. Effect of palovarotene on TGF-β production in AGE-stimulated mouse mesangial cells. Each group was treated with (1) no stimulation; (2) AGE 300 μg/ml; (3) AGE 300 μg/ml+palovarotene 0.5 μM; or (4) AGE 300 μg/ml+ palovarotene 1 µM. Twenty-four hours after the treatment, RNA extraction was performed by AGPC method.
Figure 2B:
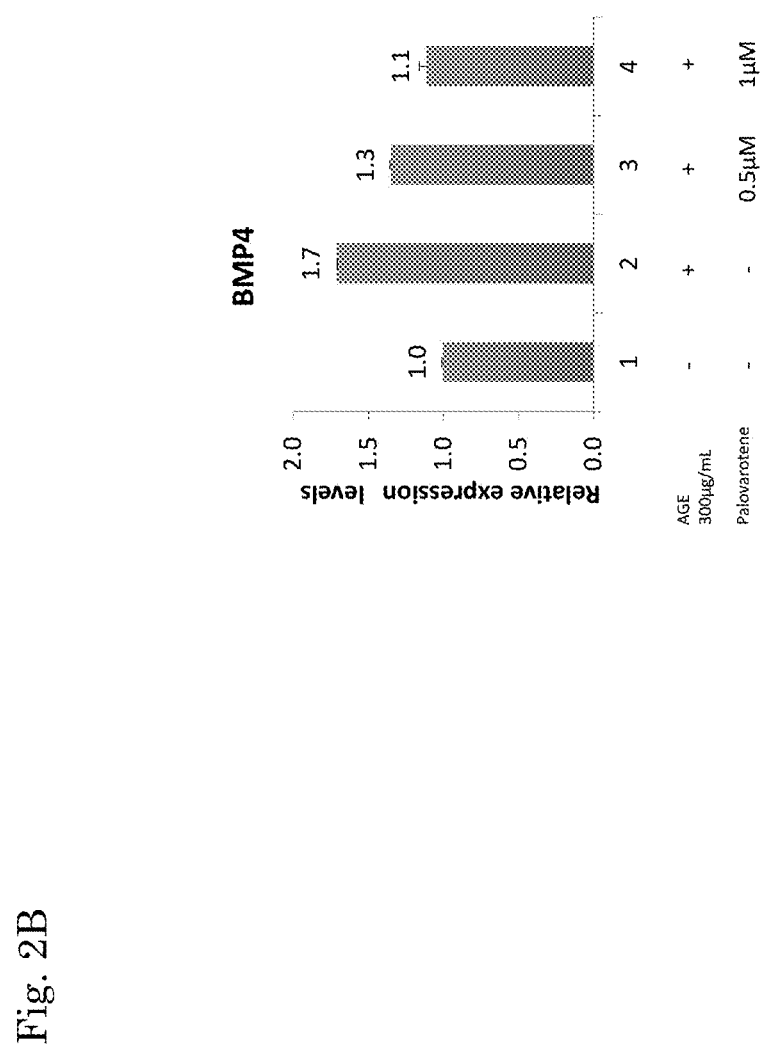

FIG. 2B. Effect of palovarotene on BMP4 production in AGE-stimulated mouse mesangial cells. Each group was treated with (1) no stimulation; (2) AGE 300 µg/ml; (3) AGE 300 µg/ml+palovarotene 0.5 µM; or (4) AGE 300 µg/ml+palovarotene 1 µM. Twenty-four hours after the treatment, RNA extraction was performed by AGPC method.

Figure 2C:
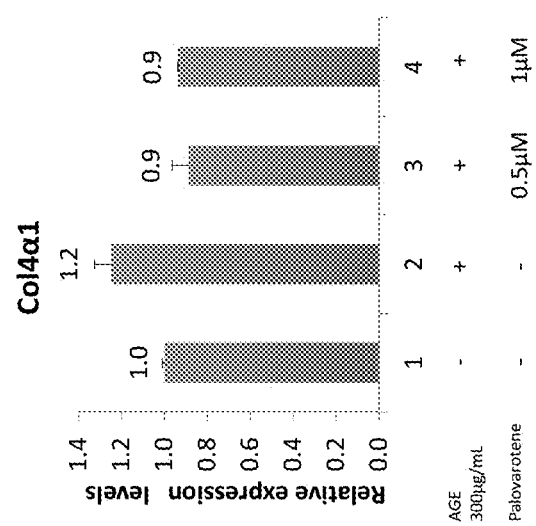

FIG. 2C. Effect of palovarotene on type IV collagen (Col4α1) production in AGE-stimulated mouse mesangial cells. Each group was treated with (1) no stimulation; (2) AGE 300 µg/ml; (3) AGE 300 µg/ml+palovarotene 0.5 µM; or (4) AGE 300 µg/ml+palovarotene 1 µM. Twenty-four hours after the treatment, RNA extraction was performed by AGPC method.

Figure 3:
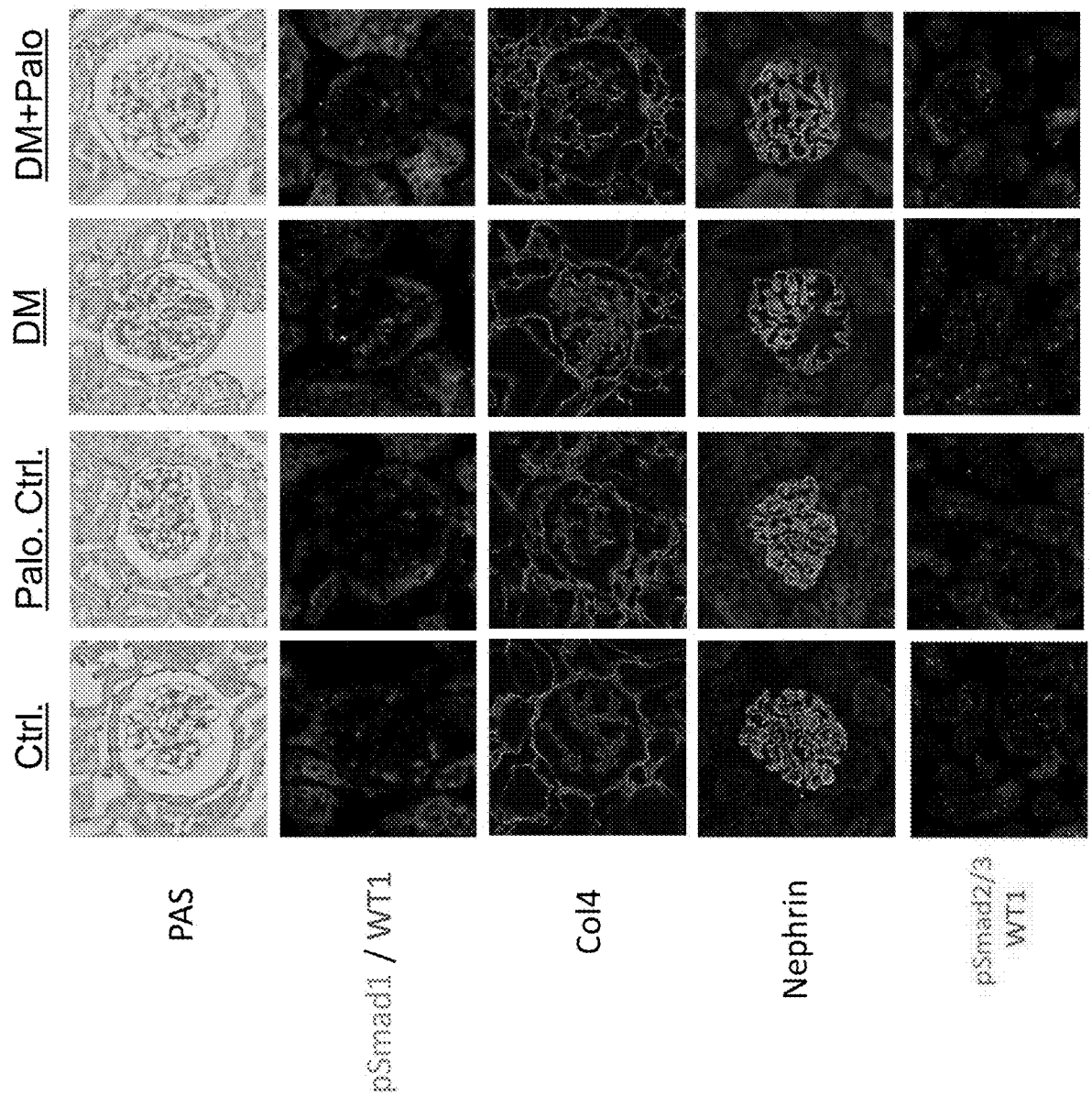

FIG. 3. Effect of palovarotene on streptozocin-induced diabetic mice. (1) "Ctrl." represents the results of tissue dissection of control mice. (2) "Palo.Cntl." represents the results of tissue dissection of – control mice administered with palovarotene. (3) "DM" represents the results of tissue dissection of mice in which diabetes was induced by streptozotocin injection. (4) "DM+Palo" represents the results of tissue dissection of mice which received palovarotene after induction of diabetes by streptozotocin injection.

Figure 4:
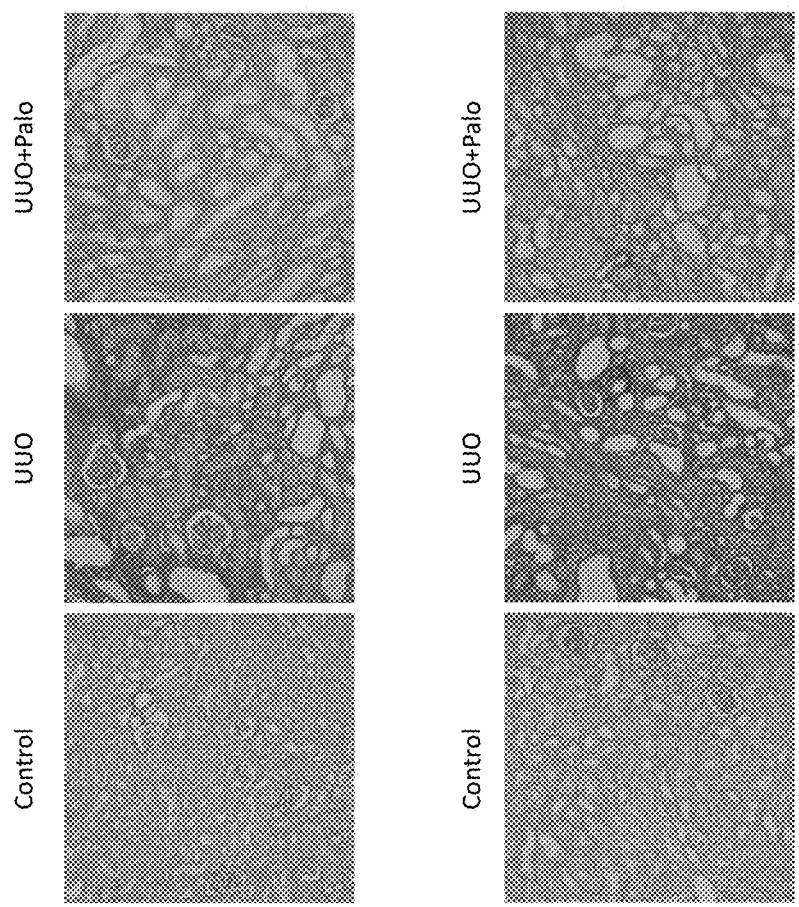

FIG. 4. Effect of palovarotene on unilateral ureter obstruction (UUO) mice as a renal tubulointerstitial fibrosis model. Control: the results of histological evaluation by Sirius Red staining of the kidney from those mice which did not receive ureter ligation. UUO: the results of histological evaluation by Sirius Red staining of the kidney from those mice in which renal tubulointerstitial fibrosis was caused by keeping them for 7 days after ureter ligation. UUO+Palo: the results of histological evaluation by Sirius Red staining of the kidney from those mice to which palovarotene (1 mg/kg) was administered intraperitoneally for 6 days starting from one day after ureter ligation.

DESCRIPTION OF THE PREFERRED EMBODIMENTS

Hereinbelow, the present invention will be described in detail.

The present invention provides a prophylactic and/or therapeutic drug for diabetic nephropathy, comprising a RARγ agonist as an active ingredient.

The RARγ agonist may be one having an effect of inhibiting BMP4/ALK3/Smad1/type IV collagen signaling pathways.

As used herein, the term "BMP4/ALK3/Smad1/type IV collagen signaling pathways" refers to pathways in which BMP4 binds ALK3/BMPRII (type II receptor of BMP) and phosphorylates Smad1 to thereby elicit the production of type IV collagen.[16] A specific example is described below. Briefly, culturing of mesangial cells in the presence of AGEs (advanced glycation end products) increases the production of BMP4 (bone morphogenetic protein 4). Subsequently, when BMP4 binds ALK3/BMPRII receptor on mesangial cells, phosphorylation of Smad1 occurs. Two molecules of phosphorylated Smad1 and one molecule of Smad4 form a trimer, which transits from the cytoplasm into the nucleus, initiating the transcription of type IV collagen, one of its target genes. Since this production of type IV collagen is known to be the most critical factor in mesangial matrix expansion, a compound that inhibits the BMP4/ALK3/Smad1/type IV collagen signaling pathways is believed to be a potential prophylactic/therapeutic drug for diabetic nephropathy. Therefore, the present invention provides a drug that inhibits the expression of type IV collagen in mesangial cells, comprising a RARγ agonist as an active ingredient. The present invention also provides a drug that inhibits the expression of BMP4 in mesangial cells, comprising a RARγ agonist as an active ingredient.

Further, the present invention provides a prophylactic and/or therapeutic drug for diabetic nephropathy, in particular, diabetes-induced tubulointerstitial lesions (especially fibrosis), comprising a RARγ agonist as an active ingredient.

The RARγ agonist may have an effect of inhibiting signals associated with TGF-β/Smad2/3/ECM signaling pathways.

As used herein, the term "TGF-β/Smad2/3/ECM signaling pathways" refers to pathways in which TGF-β secreted from glomerulus constituting cells and renal tubule constituting cells, which was caused by hyperglycemia or AGEs, binds TGF-β receptor to thereby promote the phosphorylation of Smad2/3 to induce excessive accumulation of extracellular matrix (ECM) protein and cause tubulointerstitial fibrosis. It is believed that Smad2/3, which is phosphorylated by TGF-β stimulation, functions as a nuclear transcription activator.[17] Therefore, the present invention provides a drug that inhibits fibrosis in the renal tubulointerstitium, comprising a RARγ agonist as an active ingredient. This drug may be one that inhibits the expression of pSmad2/3 in the renal tubulointerstitial cells. Fibrosis in the renal tubulointerstitium may be derived from diabetic nephropathy.

A mechanism common to both the progress of interstitial fibrosis and development of renal anemia has recently been assumed because fibroblasts constituting lesions of tubulointerstitial fibrosis (at least part of such fibroblasts) are derived from erythropoietin (EPO) producing cells and lose their EPO production capacity upon transformation into fibroblasts.[14] According to this hypothesis, it is believed that a prophylactic and/or therapeutic drug for interstitial fibrosis can potentially be an effective prophylactic and/or therapeutic drug for renal anemia. Therefore, the present invention also provides a prophylactic and/or therapeutic drug for renal anemia, comprising a RARγ agonist as an active ingredient.

Diabetic nephropathy may be nephropathy derived from type 2 diabetes. However, the scope of the present invention is not limited to such nephropathy. The present invention is applicable to prevention and/or treatment of nephropathy derived from each type of diabetes.

As regards the RARγ agonist pertaining to the present invention, specific examples include, but are not limited to, 4-[(E)-2-[5,5,8,8-tetramethyl-3-(pyrazol-1-ylmethyl)-6,7-dihydronaphthalen-2-yl]ethenyl]benzoic acid (palovarotene) represented by formula (I) below; 6-[3-(1-adamantyl)-4-hydroxyphenyl]-2-naphthalene carboxylic acid (0-Desmethyl Adapalene) represented by formula (II) below; 3-fluoro-4-(2-hydroxy-2-(5,5,8,8-tetramethyl-5,6,7,8,-tetrahydronaphthalen-2-yl)acetamido)benzoic acid (BMS 189961) represented by formula (III) below; 4-[7-(1-adamantyl)-6-hydroxynaphthalen-2-yl]benzoic acid (CD1530) represented by formula (IV) below; esters of these compounds (palovarotene, 0-Desmethyl Adapalene, BMS189961 and CD1530); and salts of these compounds (palovarotene, 0-Desmethyl Adapalene, BMS189961 and CD1530).

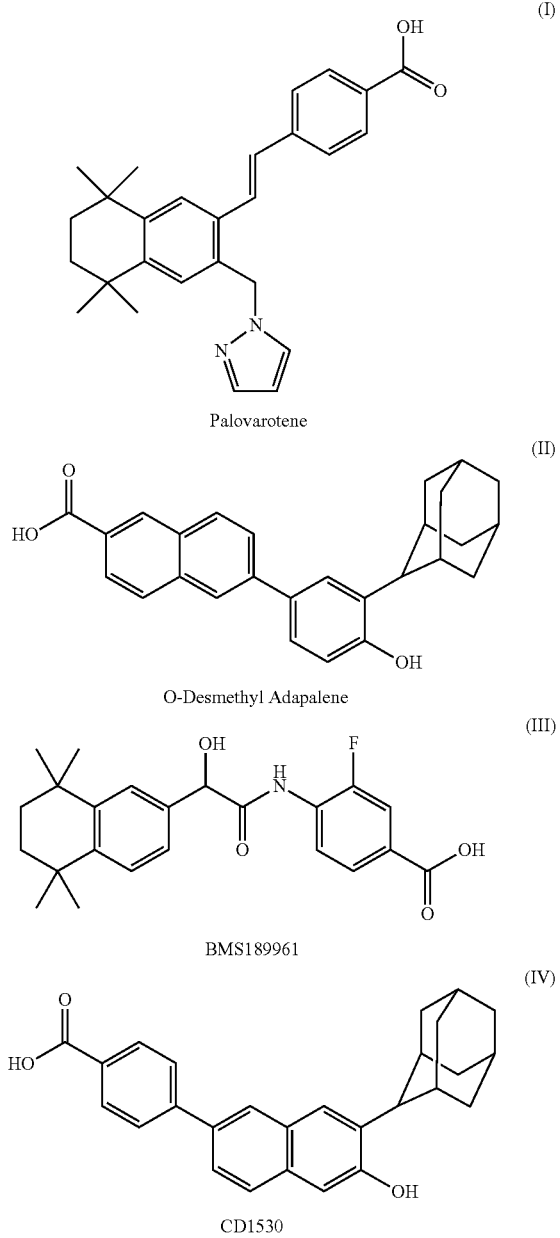

Palovarotene (I)

O-Desmethyl Adapalene (II)

BMS189961 (III)

CD1530 (IV)

Other embodiments of the present invention include a method of preventing/treating diabetic nephropathy, comprising administering a RARγ agonist to a subject; a RARγ agonist for use as a prophylactic and/or therapeutic drug for diabetic nephropathy; and use of a RARγ agonist in preparing a prophylactic and/or therapeutic drug for diabetic nephropathy.

Still other embodiments of the present invention include, but are not limited to, a method of preventing/treating renal anemia, comprising administering a RARγ agonist to a subject; a RARγ agonist for use as a prophylactic and/or therapeutic drug for renal anemia; and use of a RARγ agonist in preparing a prophylactic and/or therapeutic drug for renal anemia.

The compounds which are useful as the active ingredient of the prophylactic and/or therapeutic drug for diabetic nephropathy and/or renal anemia of the present invention are known compounds disclosed in literature. Briefly, palovarotene is disclosed in Patent Document No. 5; 0-Desmethyl Adapalene is disclosed in Sun S Y. et al., Cancer Research (2002)[13] and Patent Document No. 8; BMS189961 is disclosed in Patent Document No. 8; and CD1530 is disclosed in Shimono K. et al., Nat Med. 17(4): 454-460 (2011)[14]. These compounds, esters thereof or salts thereof may be prepared according to conventional methods. Alternatively, they may be purchased as commercial products. Palovarotene used in Examples 1-4 described later was purchased from Toronto Research Chemicals; 0-Desmethyl Adapalene used in Example 4 described later was purchased from Toronto Research Chemicals; BMS189961 used in Example 4 described later was purchased from Axon Medchem; and CD1530 used in Example 4 described later was purchased from ApexBio.

The esters in the expression "esters of RARγ agonist which is the active ingredient of the prophylactic and/or therapeutic drug for diabetic nephropathy and/or renal anemia of the present invention" are not particularly limited. Any ester may be used as long as it is converted into a RARγ agonist under in vivo physiological conditions through reactions with enzymes or the like. Specific examples of such esters include, but are not limited to, esters derived from primary alcohols such as methanol, ethanol, propanol, hexanol or dodecanol; esters derived from secondary alcohols such as isopropanol, s-butanol or 1-ethylpropanol; esters derived from tertiary alcohols such as t-butanol or 1-methyl-1-ethylpropanol; and esters derived from amino alcohols such as 2-aminoethanol.

The esters listed above may be prepared from RARγ agonists or synthetic intermediates thereof by conventional methods.

The salts in the expression "salts of RARγ agonist which is the active ingredient of the prophylactic and/or therapeutic drug for diabetic nephropathy and/or renal anemia of the present invention" are not particularly limited. Any salt may be used as long as it is a pharmaceutically acceptable salt. Specific examples of such salts include, but are not limited to, (1) acid addition salts including inorganic acid salts such as hydrochloric acid salt, hydrobromic acid salt, hydroiodic acid salt, nitric acid salt, sulfuric acid salt or phosphoric acid salt; or organic acid salts such as acetic acid salt, trifluoroacetic acid salt, benzoic acid salt, oxalic acid salt, malonic acid salt, succinic acid salt, maleic acid salt, fumaric acid salt, tartaric acid salt, citric acid salt, methanesulfonic acid salt, ethanesulfonic acid salt, trifluoromethanesulfonic acid salt, benzenesulfonic acid salt, p-toluenesulfonic acid salt, glutamic acid salt or aspartic acid salt; or (2) basic salts including metal salts such as sodium salt, potassium salt, calcium salt or magnesium salt; inorganic salts such as ammonium salt; or organic amine salts such as trimethylamine salt or guanidine salt.

The prophylactic and/or therapeutic drug for diabetic nephropathy and/or renal anemia of the present invention may be administered orally or parenterally (e.g., intravenous, intramuscular, intraperitoneal, transdermal, transtracheal, intradermal or subcutaneous administration) in the form of tablets, capsules, powders, syrups, granules, fine granules, pills, liquid preparations, suspensions, emulsions, percutaneous absorbents, suppositories, ointments, lotions, inhalants, injections or the like which may be prepared by mixing with appropriate, pharmacologically acceptable additives. For example, compositions for oral administration include solid or liquid preparations such as tablets (including sugar-coated tablets and film-coated tablets), pills, granules, powders, capsules (including soft capsules), syrups, emulsions and suspensions. These compositions may be prepared according to conventional methods and may contain carriers, diluents or excipients conventionally used in the field of medicine manufacture. For example, lactose, starch, sucrose, magnesium stearate and the like may be used as carriers or excipients for tablets.

Compositions for parenteral administration include, for example, injections and suppositories. Injections include intravenous injections, subcutaneous injections, intradermal injections, muscle injections, instilment injections, etc. Such injections may be prepared by conventional methods, i.e., by dissolving, suspending or emulsifying a RARγ agonist in an aseptic, aqueous or oily liquid conventionally used in injections. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80™, HCO-50 (polyoxyethylene (50 mol) adduct of hydrogenated castor oil)], etc. Examples of oily liquids for injection include sesame oil and soybean oil. They may be used in combination with an auxiliary solubilizer such as benzyl benzoate, benzyl alcohol, etc. Usually, the prepared injections are filled in appropriate ampoules. Suppositories for administration into the rectum may be prepared by mixing an active ingredient with a conventional suppository base.

The above-described pharmaceutical compositions for oral or parenteral administration may advantageously be formulated into unit dosage forms that would give an appropriate dose of the active ingredient. Examples of such unit dosage forms include tablets, pills, capsules, injections (ampoules), and suppositories.

These formulations may be prepared by well-known methods using additives such as excipients, lubricants, binders, disintegrants, emulsifiers, stabilizers, flavoring agents or diluents.

As excipients, organic excipients and inorganic excipients may be used. Examples of organic excipients include sugar derivatives such as lactose, sucrose, glucose, mannitol or sorbitol; starch derivatives such as corn starch, potato starch, α-starch or dextrin; cellulose derivatives such as crystalline cellulose; gum arabic; dextran; or pullulan. Inorganic excipients include light silicic anhydride; and sulfates such as calcium sulfate.

As lubricants, examples include, but are not limited to, stearic acid; metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; D,L-leucine; sodium lauryl sulfate; silicates such as silicic anhydride or silicic hydrate; or the starch derivatives listed above for excipients.

As binders, examples include, but are not limited to, hydroxypropylcellulose, hydroxypropylmethylcellulose, polyvinylpyrrolidone, macrogol, or the compounds listed above for excipients.

As disintegrants, examples include, but are not limited to, cellulose derivatives such as low-substituted hydroxypropylcellulose, carboxymethylcellulose, calcium carboxymethylcellulose or internally crosslinked calcium carboxymethylcellulose; crosslinked polyvinylpyrrolidone; and chemically modified starch/cellulose derivatives such as carboxymethylstarch or sodium carboxymethylstarch.

As emulsifiers, examples include, but are not limited to, colloidal clay such as bentonite or veegum; anionic surfactants such as sodium lauryl sulfate; cationic surfactants such as benzalkonium chloride; and nonionic surfactants such as polyoxyethylenealkylether, polyoxyethylene sorbitan fatty acid ester or sucrose esters of fatty acids.

As stabilizers, examples include, but are not limited to, parahydroxybenzoate esters such as methylparaben or propylparaben; alcohols such as chlorobutanol, benzyl alcohol or phenylethyl alcohol; benzalkonium chloride; phenols such as phenol or cresol; thimerosal; acetic anhydride; or sorbic acid.

As flavoring agents, examples include, but are not limited to, sweeteners such as saccharin sodium or aspartame; acidifiers such as citric acid, malic acid or tartaric acid; and aromatics such as menthol, lemon essence or orange essence.

Diluents may be those compounds which are ordinarily used as diluents. Examples of diluents include, but are not limited to, lactose, mannitol, glucose, sucrose, calcium sulfate, hydroxypropylcellulose, microcrystalline cellulose, water, ethanol, polyethylene glycol, propylene glycol, glycerol, starch, polyvinylpyrrolidone or mixtures thereof.

The dose of the prophylactic and/or therapeutic drug for diabetic nephropathy and/or renal anemia of the present invention may be varied appropriately depending on the dosage form; the severity of the symptoms, age and body weight of the patient to be treated; judgement of the doctor in charge; etc. In the case of an oral preparation, it may be administered to an adult in a daily dose of typically 0.01-5000 mg, preferably 0.1-2500 mg, more preferably 0.5-1000 mg in terms of the amount of the active ingredient, either once a day or several times a day in divided portions.

The prophylactic and/or therapeutic drug for diabetic nephropathy and/or renal anemia of the present invention is not particularly limited as long as the drug comprises a RARγ agonist as the active ingredient. Since RARγ agonists represented by palovarotene inhibit expressions of TGF-β, BMP4 and Col4α1, they are expected to inhibit mesangial matrix expansion.

Based on the above-mentioned mechanism of action, inhibitors (compounds, proteins, etc.) capable of inhibiting BMP4/ALK3/Smad1/type IV collagen signaling pathways or TGF-β/Smad2/3/ECM signaling pathways are expected to have an effect similar to that of palovarotene. For example, Zhang et al. demonstrated that Noggin is capable of inhibiting the expression of BMP4 in diabetic mice.[20] Maciel et al. showed that GREM1 is capable of inhibiting BMP4 activity.[21] Yu et al. showed that dorsomorphin is capable of inhibiting BMP4-induced Smad1 phosphorylation, and further demonstrated that dorsomorphin is capable of inhibiting BMP4 signaling pathway correlated target ALK3 or Smad1.[22] Yu et al. suggested that optimized molecule LDN-193189 inhibits the BMP4-mediated transcriptional activity of Smad1 and ALK3.[23] Xu et al. demonstrated that calmodulin inhibits the activity of Smad1 by acting on the N-terminal domain of Smad1.[24] Other studies also showed that because Smad6 inhibits Smad1-associated Runx1 activity, it inhibits the BMP4 signaling pathway.[25] On the other hand, a preceding study suggested that chondroitin-4-sulfate (C4S) is capable of inhibiting the degradation of type IV collagen.[26] Other inhibitors have also been suggested. For example, Neely et al. suggested that DMH-1 is capable of inhibiting ALK3 by replacing Noggin[27], and it was suggested that ΔSmad73TEVGR is capable of inhibiting the phosphorylation of Smad1[28]. Table 1 given below summarizes inhibitors for BMP4, ALK3, Smad1 and type IV collagen which are important target molecules associated with BMP4/ALK3/Smad1/type IV collagen signaling pathways.

TABLE 1

List of Inhibitors for BMP4/ALK3/Smad1/Type IV
Collagen Signaling Pathway Correlated Signals

| BMP4/ALK3/Smad1/Type IV Collagen Signaling Pathway Correlated Signals | Molecules and Signals that inhibited BMP4/ALK3/Smad1/Type IV Collagen Signaling Pathway Correlated Signals |
|---|---|
| BMP4 | Noggin, GREM1, Dorsomorphin, Smad6 |
| ALK3 | LDN-193189, Dorsomorphin, DMH-1 |
| Smad1 | Calmodulin, LDN193189, Dorsomorphin, DMH1, ΔSmad73TEVGR |
| Type IV Collagen | Crystallized structure of type IV collagen NC1 domain hexamer (U.S. Pat. No. 7,122,517), C4S |

On the other hand, Bourgeois et al. showed that overexpression of MAN1 elicits dephosphorylation of Smad2 and Smad3.[29] Table 2 given below summarizes inhibitors for TGF-β/Smad2/3/ECM signaling pathways.

TABLE 2

List of Inhibitors for TGF-β/Smad2/3/ECM Signaling Pathways

| TGF-β/Smad2/3/ECM Signaling Pathway Correlated Signals | Molecules and Signals that inhibited TGF-β/Smad2/3/ECM Signaling Pathway Correlated Signals |
|---|---|
| TGF-β receptor | CultureSure™ A 83-01[30], D44763[31], LY364947[32], SB431542[33], SB525334[34], SD208[35], GW788388, LY 2157299, LY2109761, 6-[2-tert-Butyl-5-(6-methyl-pyridin-2-yl)-1H-imidazole-4-yl]-quinoxaline, EW-7197 |
| ALK5 | D4476[31], SB431542[33], SB525334[34], 2-(3-(6-METHYLPYRIDIN-2-YL)-1H-PYRAZOL-4-YL)-1,5-NAPHTHYRIDINE, 6-[2-tert-Butyl-5-(6-methyl-pyridin-2-yl)-1H-imidazol4-yl]-quinoxaline, LY-364947, 2-(5-Benzo[1,3]dioxol-5-yl-2-tert-butyl-3H-imidazol-4-yl)-6-methylpyridine hydrate hydrochloride |
| Phosphorylation of Smad2/3 | MAN1[29], SB525334[34] |

Not only the above-listed inhibitors, molecules and signals, but also other substances capable of inhibiting BMP4/ALK3/Smad1/type IV collagen signaling pathways or TGF-β/Smad2/3/ECM signaling pathways are predicted to produce the same effect as the present invention.

EXAMPLES

Hereinbelow, the present invention will be described in more detail with reference to the Examples. However, the scope of the present invention is not limited to these Examples.

Example 1. Examination of the Effect of Palovarotene on Mouse Mesangial Cells

Methods

The glomeruli were isolated from four-week-old wild-type C57BL/6J mice according to the method of Davies M. et al. (Kidney Int. 1994; 45(2):320-7)[36] with necessary modifications and primary culture of the glomeruli was conducted in order to establish mouse mesangial cell strains. AGEs used for cell stimulation were prepared according to the method of Doi T. et al. (Proc. Natl. Acad. Sci. U.S.A. 1992; 89:2873-2877)[37] with necessary modifications.

The cultured mouse mesangial cells were grown to confluence, subjected to serum starvation using Opti-MEM (Invitrogen). Then, the cells were treated with (1) no stimulation, (2) AGE 300 μg/ml; (3) AGE 300 μg/ml+palovarotene 0.5 μM; or (4) AGE 300 μg/ml+palovarotene 1 μM. Twenty-four hours after the treatment, RNA extraction was performed by AGPC method. RT-quantitative PCR was performed with the resultant RNA, followed by evaluation of mRNA expression levels by the comparative Ct method (ΔΔ Ct method). Target genes for evaluation were TGF-β1, BMP4 and Col4α1.

The results are shown in FIG. 2.

Results

Based on the finding that RAR agonists inhibit TGF-β signal transduction, the present inventors first examined whether palovarotene would inhibit increase of TGF-β expression stimulated by AGE. As shown in FIG. 2A, TGF-β expression increased by AGE stimulation was strongly inhibited.

Subsequently, based on the finding that BMP4 expression in mesangial cells is increased by AGE stimulation, the present inventors examined the effect of palovarotene on BMP4 expression. As shown in FIG. 2B, BMP4 expression increased by AGE stimulation was clearly inhibited by palovarotene in a dose dependent manner and the inhibition was almost complete at the concentration of 1 μM.

Further, the present inventors examined the effect of palovarotene on the expression of Col4α1 (type IV collagen), a causative factor for mesangial area expansion. As a result, it was revealed that the production of Col4α1 (type IV collagen) increased by AGE stimulation is completely inhibited by palovarotene even at the concentration of 0.5 μM (FIG. 2C).

From the above-mentioned results, it was suggested that palovarotene may potentially inhibit BMP4/ALK3-mediated type IV collagen expression through inhibition of BMP4 expression.

Hence, in order to examine this possibility, the present inventors evaluated in vivo effects of palovarotene using diabetic model mice.

Example 2. Examination of the Effect of Palovarotene on STZ-Induced Diabetic Mice Methods Streptozocin (Wako) was administered to 12-15 week-old ICR mice (purchased from CLEA Japan) intraperitoneally (I.P.) for five consecutive days at 50 mg/kg per injection to thereby evoke diabetes. Four weeks after the STZ administration, mouse diet was changed to a high fat diet HFD60 (Oriental Yeast) and, at the same time, intraperitoneal administration of palovarotene at 60 μg/kg twice a week was started. Twelve weeks later, the mice were dissected, followed by histological evaluation. The results are shown in FIG. 3.

Results

As shown in FIG. 3, expansion of the glomerular mesangial area (PAS staining), activation of Smad1 (pSmad1), activation of Smad2/3 (pSmad2/3) and increased expression of type IV collagen (Col4) were observed in streptozocin-administered diabetic mice (DM), compared to control mice (Ctrl). Further, reduction of nephrin (a cell adhesion molecule)-expressing area in glomerular podocytes (Nephrin) and reduction of WT1 expressed in the podocyte nuclei (WT1) were also observed. These results show that the streptozocin-administered diabetic mouse is an excellent model mouse well reflecting histopathological changes in human diabetic nephropathy.

When palovarotene was administered to these diabetic mice (DM+Palo), inhibition of expansion of the glomerular mesangial area (PAS staining), inhibition of Smd1 activation (pSmad1) and reduction of type IV collagen expression (Col4) were observed in comparison with diabetic mice (DM). Further, inhibition of reduction of nephrin-expressing area (Nephrin) and inhibition of reduction of WT1 expressed in the podocyte nuclei (WT1) were also observed.

Still further, it was also revealed that compared to diabetic mice (DM), phosphorylation of Smad2/3 was strongly inhibited when palovarotene was administered to diabetic mice (DM+Palo). Phosphorylation of Smad2/3 is a critical factor to stimulate the progression of diabetes-induced tubulointerstitial lesions. The inhibition of Smad2/3 phosphorylation by Palovarotene suggested that palovarotene may inhibit tubulointerstitial fibrosis. These results show that the prophylactic or therapeutic capacity of palovarotene for diabetic nephropathy is such that in the glomeruli, it inhibits phosphorylation of Smad1 to thereby inhibit glomerulosclerosis lesions whereas in the interstitium, it inhibits phosphorylation of Smad2/3 to thereby inhibit interstitial fibrosis.

Example 3. Effect of Palovarotene on UUO Mouse as a Renal Tubulointerstitial Fibrosis Model Methods Unilateral ureter obstruction (UUO) model is a model in which renal interstitial fibrosis is induced by feeding for seven days under ureter ligation. Briefly, the kidney of a mouse is exposed extraperitoneally by a unilateral dorsal incision. Then, ureter ligation is performed at 2 to 3 spots at intervals of 1 mm with surgical suture, which leads to decreased renal blood flow and glomerular filtration rate. Further, macrophages infiltrate into the tubulointerstitium, apoptosis of tubular epithelial cells occurs, and increase of fibroblasts and extracellular matrix protein progresses in the interstitium, which leads to interstitial fibrosis. In this model, fibrosis is evoked in a short period of time and there is no complication of uremia since no toxic substance is used. Thus, this is an interstitial fibrosis model with high reproducibility.

A UUO model was established using 10-12 week-old ICR mice (purchased from CLEA Japan). Control group consists of mice which did not undergo ureter ligation. UUO group consists of mice which were kept for 7 days under ureter ligation to thereby induce renal interstitial fibrosis. Palovarotene group consists of mice which received intraperitoneal administration of palovarotene (1 mg/kg) for 6 consecutive days starting from one day after UUO treatment. Mice in each group were dissected 7 days after UUO treatment, followed by histological evaluation of the kidney by Sirius Red staining. The representative results of tissue staining (two sections from each group) are shown in FIG. 4.

Results

As shown in FIG. 4, no tubulointerstitial fibrosis was observed in the kidney of control group mice. In the kidney of UUO mice which spent 7 days after ureter ligation, marked fibrosis in the tubulointerstitium was clearly observed because the tubulointerstitium was stained very strongly with Sirius Red. In the kidney of palovarotene group (UUO+Palo) consisting of UUO mice which received palovarotene for 6 days, the degree of staining of the tubulointerstitium with Sirius Red was clearly lower than that in the kidney tissue of UUO mice. Therefore, it was revealed that palovarotene markedly inhibits tubulointerstitial fibrosis.

According to the hypothesis that fibroblasts constituting lesions of tubulointerstitial fibrosis are derived from EPO producing cells and lose their EPO producing capacity during transformation into fibroblasts[14], it is believed that palovarotene may potentially serve not only as a prophylactic and/or therapeutic drug for tubulointerstitial fibrosis but also as an effective prophylactic and/or therapeutic drug for renal anemia.

Example 4. Comparison of the Effects of Four Types of RARγ Agonists on Mouse Mesangial Cells Methods The present inventors have compared the inhibittory effects of four types of RARγ agonists (palovarotene, 0-Desmethyl Adapalene, BMS189961 and CD1530) on the expressions of TGF-β1, BMP4 and Col4α1 according to the method described in Example 1.

Results

The results are shown in relative values, taking the value for "AGE 300 µg/ml+Palovarotene 0.5 µM" as 100%.

First, the inhibitory effects of RARγ agonists on TGF-β1 expression were examined. As shown in Table 3, palovarotene exhibited a dose-dependent inhibitory effect. Although CD1530 also exhibited a dose-dependent inhibitory effect, its effect was weaker than that of palovarotene. The inhibitory activities of Desmethyl Adapalene and BMS189961 were weaker than that of palovarotene.

Subsequently, inhibitory effects on BMP4 expression were examined. As shown in Table 3, palovarotene showed a dose-dependent inhibitory effect. However, the other three compounds possessed weaker inhibitory activities than palovarotene.

Further, inhibitory effects on Col4α1 (type IV collagen) expression were examined. As shown in Table 3, palovarotene showed a dose-dependent inhibitory effect. Although CD1530 also possessed a dose-dependent inhibitory effect, its effect was weaker than that of palovarotene. On the other hand, 0-Desmethyl Adapalene showed a dose-dependent stimulatory effect on Col4α1 (type IV collagen) expression. The inhibitory effect of BMS189961 was weaker than that of palovarotene.

TABLE 3

Comparison of the Inhibitory Effects of Four Types of RAR γ Agonists on theExpression of TGF-β1 BMP4 and Col4α1

| Administered Compounds | TGF-β1 (%) | BMP4 (%) | Col4α1 (%) |
| --- | --- | --- | --- |
| AGE 300 µg/ml + Palovarotene 0.5 µM | 100 | 100 | 100 |
| AGE 300 µg/ml + Palovarotene 1.0 µM | 70 | 60 | 50 |
| AGE 300 µg/ml + O-Desmethyl Adapalene 0.5 µM | 100 | 160 | 75 |
| AGE 300 µg/ml + O-Desmethyl Adapalene 1.0 µM | 130 | 220 | 138 |
| AGE 300 µg/ml + BMS189961 0.5 µM | 120 | 200 | 125 |
| AGE 300 µg/ml + BMS189961 1.0 µM | 140 | 180 | 125 |
| AGE 300 µg/ml + CD1530 0.5 µM | 110 | 180 | 138 |
| AGE 300 µg/ml + CD1530 1.0 µM | 90 | 180 | 88 |

From the results of Examples 1, 2, 3 and 4, it is clear that among the four RARγ agonists tested, palovarotene possessed the strongest and dose-dependent inhibitory effect on expression of TGF-β1, BMP4 and Col4α1 (type IV collagen) which are factors associated with the progress of diabetic nephropathy. Therefore, it is believed that palovarotene is promising as a prophylactic and/or therapeutic drug for diabetic nephropathy.

REFERENCES CITED

1. Doi T, Vlassara H, Kirstein M, Yamada Y, et al. Receptor-specific increase in extracellular matrix production in mouse mesangial cells by advanced glycosylation end-products is mediated via platelet derived growth factor. Proc Natl Acad Sci USA 1992; 89:2873-2877.
2. Abe H, Matsubara T, Iehara N, et al. Type IV collagen is transcriptionally regulated by Smad1 under advanced glycation end product (AGE) stimulation. J Biol Chem 2004; 279:14201-14206.
3. Matsubara T, Abe H, Arai H, et al. Expression of Smad1 is directly associated with glomerulosclerosis in diabetic nephropathy. Lab Invest 2006; 86:357-68.
4. Mima A, Matsubara T, Arai H, et al. Angiotensin II-dependent Src and Smad1 signaling pathway is crucial for the development of diabetic nephropathy. Lab Invest 2006; 86:927-939.
5. Ohashi S, Abe H, Takahashi T, et al. Advanced glycation end products increase collagen-specific chaperone protein in mouse diabetic nephropathy. J Biol Chem 2004; 279: 19816-23.
6. Takahashi T, Abe H, Arai H, et al. Activation of STAT3/Smad1 is a key signaling pathway for progression to glomerulosclerosis in experimental glomerulonephritis. J Biol Chem 2005; 280:7100-7106.
7. Tominaga T, Abe H, Ueda O, et al. Activation of BMP4 signaling leads to glomerulosclerosis that mimics diabetic nephropathy. J Biol Chem 2011; 286:20109-20116.
8. Kishi S, Abe H, Akiyama H, et al. Sox9 protein induces a chondrogenic phenotype of mesangial cells and contributes to advanced diabetic nephropathy. J Biol Chem 2011; 286:32162-32169.
9. Abe H, Tominaga T, Matsubara T, et al. Scleraxis modulates bone morphogenetic protein 4 (BMP4)-Smad1-smooth muscle α-actin (SMA) signal transduction in diabetic nephropathy. J Biol Chem 2012; 287:20430-42.
10. Matsubara T, Araki M, Abe H, et al. Bone morphogenetic protein 4 and Smad1 mediate extracellular matrix production in the development of diabetic nephropathy. Diabetes 2015, 64(8):2978-90.
11. Tominaga T, Abe H, Ueda O, et al. Activation of BMP4 signaling leads to glomerulosclerosis that mimics diabetic nephropathy. J Biol Chem 2011; 286:20109-20116.
12. Pendaries V, Verrcchia F, Michel S, et al. Retinoic acid receptors interfere with the TGF-β/Smad signaling pathway in a ligand-specific manner. Oncogene 2003; 22:8212-8220.
13. Khalil H, Kanisicak O, Prasad V, et al. Fibroblas-specific TGF-β-Smad2/3 signaling underlies cardiac fibrosis. The journal of Clinical Investigation 2017; 127(10):3770-3783.
14. Okada K, Renal Diseases and Fibrosis, Journal of the Japanese Society of Internal Medicine 2015, 104(8): 1658-1664
15. Watanabe N et al., Diabetic Nephropathy, Journal of Kyoto Prefectural University of Medicine 2017; 126(10): 685-695.
16. Abe H et al., Molecular Pathology of Onset/Progress of Diabetic Nephropathy, Journal of the Japanese Society of Internal Medicine 2008; 97(4):122-128
17. Shibuya K, Molecular Mechanism of TGF-β Intracellular Signal Transduction, Chemistry and Organisms Vol. 35 (7); 477-482
18. Sun S Y et al. The synthetic retinoid CD437 selectively induces apoptosis in human lung cancer cells while sparing normal human lung epithelial cells. Cancer Research 2002; 62(8): 2430-2436.
19. Shimono K, Tung W, Macolino C, et al. Potent inhibition of heterotopic ossification by nuclear retinoic acid receptor-[gamma] agonists. Nature medicine 2011; 17:454-460.
20. Zhang Y, Liu J, Tian X Y, et al. Inhibition of bone morphogenic protein 4 restores endothelial function in db/db diabetic. Arteriosclerosis, Thrombosis, and Vascular Biology 2014; 34:152-159.
21. Maciel T T, Melo R S, Schor N, et al. Gremlin promotes vascular smooth muscle cell proliferation and migration. J Mol Cell Cardiol 2008; 44:370-9.
22. Yu P B, Hong C C, Sachidanandan C, et al. Dorsomorphin inhibits BMP signals required for embryogenesis and iron metabolism. Nature Chemical Biology 2008; 4(1): 33-41.
23. Yu P B, Deng D Y, Lai C S, et al. BMP type I receptor inhibition reduces heterotopic ossification. Nature Medicine 2008; 14:1363-1369.
24. Xu R H, Lechleider R J, Shih H M, et al. Functional Analysis of Human Smad1: Role of the Amino-Terminal Domain. Biochemical and Biophysical Research Communications 1999; 258(2): 366-373.
25. Pimanda J E, Donaldson I J, Bruijn M F T R, et al. The SCL transcriptional network and BMP signaling pathway interact to regulate RUNX1 activity. Proceedings of the National Academy of Sciences of the United States of America 2007; 104(3): 840-845.
26. Novinec M, Lenarcic B, Turk B. Cysteine cathepsin activity regulation by glycosaminoglycans. Biomed Research Intnational 2014; doi: 10.1155/2014/309718.
27. Neely M D, Litt M J, Tidball A M, et al. DMH1, a highly selective small molecule BMP inhibitor promotes neurogenesis of hiPSCs: Comparison of PAX6 and SOX1 expression during neural induction. ACS Chemical Neuroscience 2012; 3(6):482-491.
28. Wawersik S, Evola C, Whitman M, et al. Conditional BMP inhibition in *Xenopus* reveals stage-specific roles for BMPs in neural and neural crest induction. Developmental Biology 2005; 277(2):425-442.
29. Bourgeois B, Gilquin B, Tellier-Lebegue C, et al. Inhibition of TGF-β signaling at the nuclear envelope: Characterization of interactions between MAN1, Smad2 and Smad3, and PPM1A. Science Signaling 2013; 6(280): ra49.
30. Li W, Wei W, Zhu S, et al. Generation of rat and human induced pluripotent stem cells by combining genetic reprogramming and chemical inhibitors. Cell Stem Cell 2009; 4(1):16-19.
31. Rena G, Bain J, Elliott M, et al. D4476, a cell permeant inhibitor of CK1, suppresses the site – specific phosphorylation and nuclear exclusion of FOXO1a. EMBO report 2004; 5(1): 60-65
32. Sawyer J S, Anderson pubs.acs.org/doi/abs/10.1021/jm0205705-jm0205705AF10 BD, Beight D B, et al. Synthesis and activity of new Aryl- and heteroaryl-substituted pyrazole inhibitors of the transforming growth factor-0 type I receptor kinase domain. Journal of Medicinal Chemistry 2003; 46(19):3953-3956.

33. Ogawa K, Saito A, Matsui H, et al. Activin-Nodal signaling is involved in propagation of mouse embryonic stem cell. Journal of Cell Science 2007; 120: 55-65.
34. Grygielko E T, Martin W M, Tweed C, et al. Inhibition of gene markers of fibrosis with a novel inhibitor of transforming growth factor-0 type I receptor kinase in puromycin induced nephritis. The journal of pharmacology and Experimental Therapeutics 2005; 313(3): 943-951.
35. Kapoun A M, Gaspar N J, Wang Y, et al. Transforming growth factor-0 receptor type 1 (TGFRI) kinase activity but not p38 activation is required for TGF RI-induced myofibroblast differentiation and profibrotic gene expression. Molecular Pharmacology 2006; 70(2): 518-531.
36. Davies M. The mesangial cell: A tissue culture view. Kidney International 1994; 45(2):320-327.
37. Doi T, Vlassara H, Kirstein M, et al. Receptor-specific increase in extracellular matrix production in mouse mesangial cells by advanced glycosylation end products is mediated via platelet-derived growth factor. Proc. Natl Acad Sci. USA. 1992; 89:2873-2877.

Patent Document No. 1: WO 2014/073209
Patent Document No. 2: Domestic Re-Publication of PCT International Publication No. 2007/037188
Patent Document No. 3: US Publication of Patent Application No. 20160120843
Patent Document No. 4: WO 2014/188716
Patent Document No. 5: WO 2002/028810
Patent Document No. 6: WO 2008/057930
Patent Document No. 7: US Publication of Patent Application No. 20140363402
Patent Document No. 8: Japanese Unexamined Patent Publication No. 2013-536855

INDUSTRIAL APPLICABILITY

The present invention is applicable to prevention and/or treatment of diabetic nephropathy. Further, RARγ agonists (e.g. palovarotene) are also useful in inhibiting glomerular mesangium expansion, Smad1 activation and type IV collagen expression.

What is claimed is:

1. A method of treating diabetic nephropathy in a subject in need thereof, comprising administering an effective amount of an RARγ agonist to the subject, wherein the RARγ agonist comprises palovarotene, ester thereof or salt thereof.
2. The method according to claim 1, wherein diabetic nephropathy is derived from type 2 diabetes.
3. The method according to claim 2, wherein the subject has renal anemia.
4. The method according to claim 2, wherein the method suppresses expression of type IV collagen in mesangial cells in the subject.
5. The method according to claim 2, wherein the method suppresses expression of BMP4 in mesangial cells in the subject.
6. The method according to claim 2, wherein the method suppresses fibrosis in renal tubulointerstitium.
7. The method according to claim 2, wherein the RARγ agonist consists of palovarotene.
8. The method according to claim 2, wherein the RARγ agonist comprises the salt of palovarotene, and the salt is at least one selected from the group consisting of hydrochloric acid salt, hydrobromic acid salt, hydroiodic acid salt, nitric acid salt, sulfuric acid salt, phosphoric acid salt, acetic acid salt, trifluoroacetic acid salt, benzoic acid salt, oxalic acid salt, malonic acid salt, succinic acid salt, maleic acid salt, fumaric acid salt, tartaric acid salt, citric acid salt, methanesulfonic acid salt, ethanesulfonic acid salt, trifluoromethanesulfonic acid salt, benzenesulfonic acid salt, p-toluenesulfonic acid salt, glutamic acid salt or aspartic acid salt, sodium salt, potassium salt, calcium salt, magnesium salt, ammonium salt, trimethylamine salt, or guanidine salt.
9. The method according to claim 2, wherein the RARγ agonist is administered by intravenous, intramuscular, intraperitoneal, transdermal, transtracheal, intradermal or subcutaneous administration.
10. The method according to claim 2, wherein the RARγ agonist is administered with at least one additive selected from the group consisting of excipients, lubricants, binders, disintegrants, emulsifiers, stabilizers, flavoring agents or diluents.
11. The method according to claim 2, wherein the RARγ agonist is administered to an adult in a daily dose of 0.5-1000 mg.
12. The method according to claim 2, wherein the RARγ agonist comprises the ester of palovarotene, and the ester is at least one selected from the group consisting of esters derived from primary alcohols; esters derived from secondary alcohols; esters derived from tertiary alcohols; and esters derived from amino alcohols.
13. The method according to claim 2, wherein the RARγ agonist comprises palovarotene.
14. The method according to claim 12, wherein the primary alcohol is selected from methanol, ethanol, propanol, hexanol or dodecanol; the secondary alcohol is selected from isopropanol, s-butanol or 1-ethylpropanol; the tertiary alcohol is selected from t-butanol or 1-methyl-1-ethylpropanol; and the amino alcohol is selected from 2-aminoethanol.
15. The method according to claim 6, which inhibits the expression of pSmad2/3 in the renal tubulointerstitial cells.
16. The method according to claim 6, wherein fibrosis in the renal tubulointerstitium is derived from diabetic nephropathy.
17. The method according to claim 2, wherein the RARγ agonist is administered orally or parenterally.

* * * * *